US00PP18027P3

(12) United States Plant Patent
Bradford

(10) Patent No.: US PP18,027 P3
(45) Date of Patent: Sep. 11, 2007

(54) PEACH TREE NAMED 'SUGARPEACH II'

(50) Latin Name: *Prunus persica*
Varietal Denomination: SUGARPEACH II

(76) Inventor: Lowell Glen Bradford, 10237 E. Mariposa Way, Le Grand, CA (US) 95333

( * ) Notice: Subject to any disclaimer, the term of this patent is extended or adjusted under 35 U.S.C. 154(b) by 43 days.

(21) Appl. No.: 11/311,234

(22) Filed: Dec. 20, 2005

(65) Prior Publication Data

US 2007/0143887 P1 Jun. 21, 2007

(51) Int. Cl.
*A01H 5/00* (2006.01)

(52) U.S. Cl. ..... Plt./197
(58) Field of Classification Search ..... Plt./197
See application file for complete search history.

(56) References Cited

U.S. PATENT DOCUMENTS

| | | | | | |
|---|---|---|---|---|---|
| PP4,295 | P | * | 8/1978 | Merrill et al. | Plt./197 |
| PP11,199 | P | | 2/2000 | Bradford | |
| PP12,046 | P2 | * | 8/2001 | Zaiger et al. | Plt./197 |
| PP14,677 | P2 | | 4/2004 | Bradford | |
| PP16,068 | P2 | * | 10/2005 | Zaiger et al. | Plt./197 |

* cited by examiner

*Primary Examiner*—Wendy Haas

(57) ABSTRACT

The present invention relates to a peach tree, *Prunus persica,* and more particularly to a new and distinct variety characterized by a large size, vigorous, hardy, self-fertile, productive and regular bearing tree. The fruit matures under the ecological conditions described in the latter part of June, with first picking on Jun. 20, 2005. The fruit is very large in size, sub-acid and sweet in flavor, globose in shape, clingstone in type, firm in texture, yellow with some red streaking in flesh color, and full dark red in skin color. The variety was developed as a first generation cross using 'Coral Princess' white flesh peach as the selected seed parent and an unnamed white flesh nectarine as the selected pollen parent.

1 Drawing Sheet

Botanical classification: *Prunus persica.*
Variety denomination: 'SUGARPEACH II'.

BACKGROUND OF THE VARIETY

In a continuing effort to improve the quality of shipping fruits, I, the inventor, typically hybridize a large number of peach, nectarine, plum, apricot, and cherry seedlings each year. The present invention relates to a new and distinct variety of peach tree, which has been denominated varietally as 'SUGARPEACH II'. The present variety was hybridized by me in 1997, grown as a seedling on its own root in my greenhouse, and transplanted to a cultivated area of my experimental orchard near Le Grand, Calif. in Merced County (San Joaquin Valley).

The variety was developed as a first generation cross using 'Coral Princess' (U.S. Plant Pat. No. 11,199) white flesh peach as the selected seed parent and an unnamed white flesh nectarine (unpatented) as the selected pollen parent. A single tree from the stated cross was selected as the claimed variety. Subsequent to origination of the present variety of nectarine tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is similar to its selected seed parent, 'Coral Princess' (U.S. Plant Pat. No. 11,199) white flesh peach, by producing fruit that matures in mid to late June and that is globose in shape, firm in texture, and sub-acid in flavor, but differs significantly therefrom by producing fruit that is yellow in flesh color instead of white, a darker and fuller red in skin color, and larger in size.

The present variety is similar to 'Spring Candy' (U.S. Plant Pat. No. 14,677) peach by producing peaches that are yellow with some red bleeding in flesh color, sub-acid in flavor, globose in shape, and firm in texture, but is distinguished therefrom by producing peaches that are significantly larger in size and that are clingstone rather than freestone.

SUMMARY OF VARIETY

In summary, the present variety is characterized by a large size, vigorous, hardy, self-fertile, productive and regular bearing tree. The fruit matures under the ecological conditions described in the latter part of June, with first picking on Jun. 20, 2005. The fruit is uniformly large in size, sub-acid and sweet in flavor, globose in shape, clingstone in type, firm in texture, yellow with some red streaking in flesh color, and full dark red in skin color.

DRAWING

The accompanying photograph exhibits four whole fruits positioned to display the characteristics of the skin color and form, one fruit divided transversely to the suture plane to reveal the flesh and stone, two mature leaves, a blossom in full bloom in the upper inset, and an array of flowers and buds in varying stages in the lower inset.

POMOLOGICAL CHARACTERISTICS

Referring now more specifically to the pomological characteristics of this new and distinct variety of peach tree, the following has been observed under the ecological conditions prevailing near Le Grand, Merced County (San Joaquin Valley), Calif., and was developed at the state of firm ripe on Jun. 24, 2005, on the original tree during its eighth growing season. All major color code designations are by reference to the Inter-Society Color Council, National Bureau of Standards. Common color names are also used occasionally.

Tree

Size: Large, reaching a height of 11' [3.35 m.] and a spread of 11' [3.35 m.] after eight growing seasons utilizing typical dormant pruning.

Vigor: Vigorous, responding typically to irrigation and fertilization. The variety grows about 3' [0.91 m.] of surplus top-growth during the spring and summer. The plant should be grown on a standard commercial rootstock for production purpose.

Growth: Spreading and dense.

Form: Original tree was trained by pruning to be vase formed.

Hardiness: Hardy with respect to central California winters.

Heat tolerance: Observed to perform adequately in typical central California climatic conditions, which typically include extended periods of heat.

Drought tolerance: Variety is developed for commercial orchards and required regular irrigation.

Production: Productive, thinning necessary.

Fertility: Self-fertile.

Bearing: Regular bearer with no alternate bearing yet observed.

Approximate chilling requirement: 550 hours.

Trunk:

*Size.*—Medium, with a maximum diameter of 4⅝" [118 mm.] after the eighth growing season.

*Texture.*—Shaggy.

*Bark color.*—Grayish brown [61. gy.Br] with Dark reddish brown [44. d.rBr] variegation.

*Lenticels.*—Average Number Per Square Inch: 12. Color: Dark orange yellow [72. d.OY]. Size: ⅛" [3.2 mm.] to ⅜" [9.5 mm.]. Shape: eye-shaped to elongated.

Branches:

*Size.*—Diameter of main scaffold is 2¾" [70 mm.] measured 12" above the crotch, diameter of limb is 2" [51 mm.] measured 12" above the first fork.

*Texture.*—Smooth on 1st year wood, increasing roughness with age.

*Color.*—1st Year Wood Topside: Grayish red [19. gy.R]. 1st Year Wood Underside: Brilliant yellow green [116. brill.YG]. Older Wood: Deep yellowish brown [75, deep yBr].

*Lenticels.*—Approximate Number Per Square Inch: 30. Color: Dark orange yellow [72. d.OY]. Size: 1/32" [0.8 mm.] to ⅛" [3.2 mm.]. Shape: Eye-shaped to elongated.

Leaves:

*Size.*—Medium. Average Length: 5¾" [146 mm.]. Average width: 1¾" [44 mm.].

*Arrangement.*—Alternate.

*Thickness.*—Medium.

*Form.*—Elliptical.

*Apex.*—Acuminate.

*Base.*—Acute, with an average base angle of 80 degrees.

*Surface.*—Smooth.

*Color.*—Dorsal Surface: Moderate olive green [125. m.OlG]. Ventral surface: Moderate yellow green [120. m.YG].

*Margin.*—Finely serrate.

*Venation.*—Pinnately net veined.

*Petiole.*—Average Length: ⅜" [9.5 mm.]. Average Thickness: 1/16" [1.6 mm.]. Color: Brilliant yellow green [116. brill.YG].

*Stipules.*—Number: 2 to 6 per growing tip. Average Length: ¼" [6.4 mm.]. Color: Light yellow green [119. l.YG] when young, Moderate reddish brown [43. m.rBr] when older.

*Glands.*—Number: 2 to 5 per leaf. Position: Usually alternately positioned on petiole and base of leaf blade. Size: Small. Form: Globose. Color: Pale yellow green [121. p.YG] when young becoming Grayish reddish brown [46. gy.rBr] with age.

*Leaf buds.*—Medium size, pointed.

Flower buds:

*Hardiness.*—Hardy, with respect to central California winters.

*Diameter.*—Typically 5/16" [7.9 mm.] 1 week before bloom.

*Length.*—Typically ½" [12.7 mm.] 1 week before bloom.

*Form.*—Not appressed.

*Surface.*—Pubescent.

*Color.*—Light purplish pink [249. l.pPk].

Flowers: Perfect, complete, perigynous, usually a single pistil, typically thirty or more stamens, five sepals and petal locations alternately positioned.

*Type.*—Showy, large.

*Average flower diameter.*—1⅞" [47.6 mm.].

*Number of petals.*—Mostly five, with six very common.

*Petal shape.*—circular to oval.

*Petal margin.*—Somewhat wavy.

*Average petal diameter.*—¾" [19.1 mm.].

*Average petal length.*—13/16" [20.6 mm.].

*Petal apex.*—Rounded.

*Petal base.*—Irregular.

*Petal color.*—Pale pink [7. p.Pk] toward the apex, Moderate purplish pink [250. m.pPk] toward the base.

*Anther color.*—Dark red (16. d.R) over Light Yellow [86. l.Y] centers at bloom onset.

*Stigma color.*—Light greenish yellow [101. l.gY].

*Sepal color.*—Dark purplish red [259. d.pR].

*Sepal length.*—¼" [6 mm.].

*Sepal width.*—3/16" [5 mm.].

*Average pistil length.*—11/16" [17.5mm.].

*Average stamen length.*—⅝" [15.9 mm.].

*Fragrance.*—Moderate.

*Blooming period.*—Medium compared with other varieties.

*Onset of bloom.*—One percent on Feb. 17, 2005.

*Date of full bloom.*—Feb. 26, 2005.

*Duration of bloom.*—One to two weeks, dependent on ambient temperature.

*Number per cluster.*—1 to 3 with single flowers most common.

FRUIT

Maturity when described: Firm ripe, Jun. 24, 2005.

Date of first picking: Jun. 20, 2005.

Date of last picking: Jun. 30, 2005.

Size: Uniform, large.
*Average diameter axially.*—3 5/16" [84.1 mm.].
*Average diameter across suture plane.*—3¼" [82.6 mm.].
*Average diameter across check plane.*—3¼" [82.6 mm.].
*Typical weight.*—10.4 ounces [295 grams].
Form: Uniform, mostly symmetrical, globose.
*Longitudinal section form.*—Circular to oval.
*Axial view form.*—Circular.
Suture: A shallow groove extending from the stem cavity to beyond the pistil point, sharper toward both the base and apex with a marked depression beyond the pistil point and some slight stitching along the side.
Ventral surface: Rounded, lipped stronger toward the apex.
Lips: Mostly equal, but some unequal with a hump on one side.
Cavity: Flaring, elongated in the suture plane, suture showing on both sides, Light yellow [86. l.Y] stem markings typical.
*Depth.*—¾" [19.1 mm.].
*Breadth.*—1 3/16" [30.2 mm.].
Base: Truncate.
Apex: Rounded with some slightly mammiform.
Pistil point: Mostly apical, typically 1/16" [1.6 mm.] in length, usually indented within the suture.
Stem: Large.
*Average length.*—7/16" [11.1 mm.].
*Average width.*—3/16" [4.8 mm.].
Skin:
*Thickness.*—Medium.
*Texture.*—Medium.
*Tenacity.*—Tenacious to flesh.
*Astringency.*—Nonastringent.
*Tendency to crack.*—None observed.
*Color.*—Primarily Very deep red [14. v.deep R] mottled over a Moderate red orange [37. m.rO] background.
Down: Moderate, short in length, does not roll up when rubbed.
Flesh:
*Color.*—Brilliant Yellow [83. brill.Y] with sporadic Deep red [13. deep R] flecking.
*Surface of pit cavity.*—Strong pink [2. s.Pk] fibers breaking when twisted from the stone.
*Amygdalin.*—Scarce.
*Juice.*—Abundant, rich.
*Texture.*—Firm, crisp and meaty.
*Fibers.*—Abundant, fine.
*Ripens.*—Slightly earlier toward the apex and along the suture.
*Flavor.*—Mild and sub-acid, typically 15 brix.
*Aroma.*—Very slight.
*Eating quality.*—Very good.

STONE

Type: Clingstone.
Form: Oval.
Hilum: Narrow and oblong.
Base: Straight.
Apex: Acute, with an average base angle of 80 degrees.
Sides: Equal.
Surface: Irregularly furrowed along the sides becoming mostly horizontal ridges toward the apex, pitted toward base.
Ridges: Jagged toward the base.
External color: Moderate yellowish brown [77. m.yBr].
Pit wall color when cracked: Moderate yellowish brown [77. m.yBr].
Cavity surface color: Deep yellowish brown [75. deep yBr].
Average pit wall thickness: 5/16" [7.9 mm.]
Average width: 1 1/16" [27.0 mm.].
Average length: 1½" [38.1 mm.].
Average breadth: 13/16" [20.6 mm.].
Tendency to split: Moderate in 2005.
Kernel:
*Form.*—Oval.
*Pellicle color.*—Deep yellowish brown [75. deep yBr].
*Skin color.*—Pale yellow [89. p.Y] when first cracked.
*Vein color.*—Strong yellowish brown [74. s.yBr].
*Taste.*—Bitter.
*Viable.*—Yes.
*Average width.*—7/16" [11.1 mm.].
*Average length.*—13/16" [20.6 mm.].
*Amygdalin.*—Abundant.

USE

Market: Fresh market and long distance shipping.
Keeping quality: Good. Fruit quality observed to remain in good condition after 17 days in standard cold room at 36° Fahrenheit [2° Celsius].
Shipping quality: Good.
Resistance to insects: No unusual susceptibilities noted.
Resistance to diseases: No unusual susceptibilities noted.

Other Notes

Although the new variety of peach tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of peach tree, substantially as illustrated and described, that is similar to 'Spring Candy' (U.S. Plant Pat. No. 14,677) peach by producing peaches that are yellow with some red bleeding in flesh color, sub-acid in flavor, globose in shape, and firm in texture, but is distinguished therefrom by producing peaches that are significantly larger in size and the at are clingstone rather than freestone.

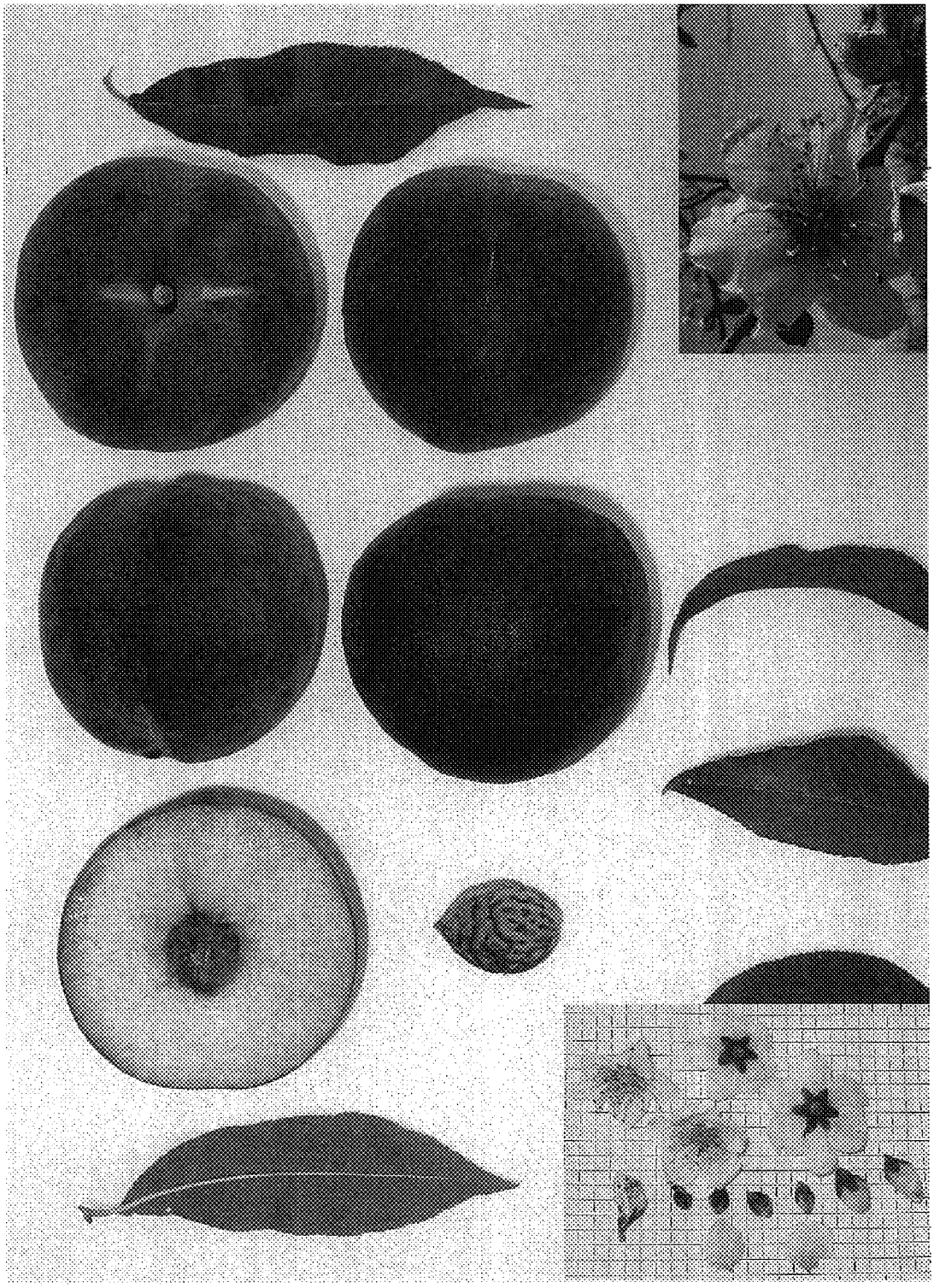

* * * * *